United States Patent [19]

Wiley

[11] Patent Number: 5,398,696

[45] Date of Patent: Mar. 21, 1995

[54] ISOMETRIC EXERCISE METHOD FOR LOWERING RESTING BLOOD PRESSURE AND GRIP DYNAMOMETER USEFUL THEREFOR

[75] Inventor: Ronald L. Wiley, Oxford, Ohio

[73] Assignee: Isatec, Inc., Galena, Ohio

[21] Appl. No.: 91,645

[22] Filed: Jul. 14, 1993

[51] Int. Cl.$^6$ ............................................. A61B 5/103

[52] U.S. Cl. ................................................... 128/774

[58] Field of Search ............... 128/676, 687, 774, 782; 33/512; 73/862

[56] References Cited

U.S. PATENT DOCUMENTS 4,949,729  8/1990  Haski .................................. 128/782

FOREIGN PATENT DOCUMENTS 8702567  5/1987  WIPO ................................. 128/782

OTHER PUBLICATIONS

Buck et al. "Isometric Occupational Exercise and the Incidence of Hypertension", J. Occup. Med., 27:370-372, 1985.
Choquette, et al. "Blood pressure Reduction in 'Borderline' Hypertensivies Following Physical Training" Can. Med. Assoc. J. 1108:699-703, 1973.
Clarke, et al., "The Duration of Sustained Contractions of the Human Forearm at Different Muscle Temperatures", J. Physiol., 143:454-473, 1958.
Gilders, et al. "Endurance training and blood Pressure in Normotensive and Hypertensive Adults", Med. Sci. Sports Exerc. 21:629-636, 1989.
Hagberg, et al. "Effect of Weight Training on Blood Pressure and Hemodynamics in Hypertensive Adolescents", J. Pediatr. 1104:147-151, 1984.
Harris, et al. "Physiological Response to Circuit Weight Training in Borderline Hypertensive Subjects", Med. Sci. Sports Exerc., 19:246-252, 1987.
Hurley, et al. "Resistive Training Can Induce Coronary Risk Factors Without Altering VO$_2$ $_{max}$ or Percent body Fat" Med. sci. Sports Exerc. 20:150-154, 1988.
Hypertension Detection and Follow-Up Program Cooperative Group, "The Effect of Treatment on Mortality in 'Mild' Hypertension", N. engl. J. Med., 307:976-980, 1982.
Kiveloff, et al., "Brief Maximal Isometric Exercise in Hypertension", J. Am. Geriatr. Socl, 9:1006-1012, 1971.
Merideth et al. "Exercise Training Lowers Resting Renal but not Cardiac sympathetic Activity in Humans", Hypertension, 18:575-582, 1991.
Seals and Hagberg, "The Effect of Exercise Training on Human Hypertension: A review", Med. Sci. Sports Exerc., 16:207-215, 1984.
Wiley, et al., "Isometric Exercise Training Lowers Resting Blood pressure", Med. sci. Sports Exerc. 29:749-754, 1992.

*Primary Examiner*—Max Hindenburg
*Attorney, Agent, or Firm*—Mueller and Smith

[57] ABSTRACT

The present invention is directed in one aspect to a protocol or method for lowering the resting systolic and diastolic blood pressures of patients. This protocol commences with a determination of the maximal isometric force which can be exerted by a patient with any given muscle (e.g., skeletal muscle or group of muscles) of such patient. The determined maximal isometric force is recorded. The patient, then, is periodically permitted to intermittently engage in isometric contraction of the given muscle at a fractional level (e.g. up to about 60%) of the maximal force determined for a given contraction duration followed by a given resting duration. A perceptible indicia correlative to the isometric force exerted by the given muscle is displayed to the patient so that the patient can sustain the given fractional level of maximal force. As another aspect of the present invention, disclosed is an apparatus for use by a patient in carrying out the foregoing protocol. This apparatus includes the dynamometer for a patient to activate with a given muscle (e.g., skeletal muscle or group of muscles). A memory is connected to the dynamometer for recording the maximal isometric force which can be exerted by the patient with any given muscle of that patient. A display is connected to the dynamometer and to the memory for displaying percentages of the recorded maximal isometric force when the patient activates the dynamometer with the given muscle. A timer is provided for the patient to ascertain the duration over which the given muscle exerts isometric force through the dynamometer and the duration between exertions.

16 Claims, 5 Drawing Sheets

ISOMETRIC EXERCISE METHOD FOR LOWERING RESTING BLOOD PRESSURE AND GRIP DYNAMOMETER USEFUL THEREFOR

BACKGROUND OF THE INVENTION

The present invention relates to the field of blood pressure and more particularly to an apparatus and method for safely reducing the resting blood pressure (both systolic and diastolic pressures) of humans and especially for those humans who are hypertensive.

Buck, et at., "Isometric Occupational Exercise and the Incidence of Hypertension", *J. Occup. Med.*, 27:370–372, 1985, show a practical application of the principle of isometric exercise influencing blood pressure. The incidence of hypertension was lower in individuals engaged in occupations that had higher components of isometric efforts. A subtle, but significant, feature of this paper is that the original hypothesis was that, since blood pressure rises during an isometric effort, a job that required repeated isometric efforts might have an accumulative effect and contribute to a sustained elevation of blood pressure. However, the investigation reported showed just the opposite result.

Choquette, et al., "Blood Pressure Reduction in 'Borderline' Hypertensives Following Physical Training", *Can. Med. Assoc. J.*, 1108:699–703, 1973, show a comparison between rhythmic and isometric exercise. While these authors showed an effect of exercise on lowering resting blood pressure, the present invention which utilizes isometric exercise lowers the blood pressure even more. Further, it has been well documented that compliance (staying with the treatment) is rather poor for rhythmic exercise. A greater percentage of people who run, jog, cycle, swim, or the like, to achieve fitness, simply quit.

Clarke, et al., "The Duration of Sustained Contractions of the Human Forearm at Different Muscle Temperatures", *J. Physiol.*, 143:454–473, 1958, show an early hand grip dynamometer which is used by patients whose arms are immersed in water for measuring the duration of sustained contractions of the human form at different muscle temperatures.

Gilders, et al., "Endurance Training and Blood Pressure in Normotensive and Hypertensive Adults", *Med. Sci. Sports. Exerc.*, 21:629–636, 1989, report a study that indicates that endurance training of the rhythmic or aerobic type does not have the benefit of lowering blood pressure, for either subjects starting with normal or with hypertensive blood pressures.

Hagberg, et al., "Effective Weight Training on Blood Pressure and Hemodynamics in Hypertensive Adolescents", *J. Pediatr.*, 1104:147–151, 1984, show that weightlifting, which has a major isometric component, although not a "pure" isometric effort, can keep blood pressure down after it was lowered by rhythmic training.

Harris, et al., "Physiological Response to Circuit Weight Training in Borderline Hypertensive Subjects", *Med. Sci. Spots Exerc.*, 19:246–252, 1987, and Hurley, et at., "Resistive Training Can Induce Coronary Risk Factors Without Altering $VO_{2max}$ or Percent Body Fat", *Med. Sci. Sports Exerc.*, 20:150–154, 1988, both deal with resistive training similar to the Hagberg, et al., publication in which there is movement, hence rhythmic effort, but where much weight is being moved, hence, "resistive" effort. This is interpreted to mean that in such a "mixed" effort, with both rhythmic and isometric components, that the isometric component is providing the real benefit in lowering resting blood pressure. In both of these papers, $VO_{2max}$ does not change. The measure of change of $VO_{2max}$ is one associated with improvement of endurance seen with rhythmic exercise. The point, then, supports contentions about isometric exercise in that resistive efforts which have a major isometric component, do not show the kind of change in $VO_{2max}$ seen typically with rhythmic or endurance exercise, yet do show the kind of lowering of resting blood pressure, though not as much, as can be obtained with only isometric exercise.

It has been reported that a reduction in blood pressure reduces the incidence of mortality in the report, Hypertension Detection and Follow-up Program Cooperative Group, "The Effect of Treatment on Mortality in 'Mild' Hypertension", *N. Engl. J. Med.*, 307:976–980, 1982. In an early paper, Kiveloff, et al., "Brief Maximal Isometric Exercise in Hypertension, *J. Am. Geriatr. Soc.*, 9:1006–1012, 1971, suggest that isometric exercise can lower blood pressure in humans. No device was used in which to perform the isometric effort, rather subjects just stood and contracted muscles of the body. No quantitative measure of the amount of isometric effort is reported. Merideth, et al., "Exercise Training Lowers Resting Renal but not Cardiac Sympathetic Activity in Humans", *Hypertension*, 18:575–582, 1991, present evidence that rhythmic exercise results in a reduction of peripheral resistance, i.e., a "relaxation" of blood vessels in the body, which would result in the lowering of blood pressure within them.

Seals and Hagberg, "The Effect of Exercise Training on Human Hypertension: A Review", *Med. Sci. Sports Exerc.*, 16:207–215, 1984, reviews 12 earlier investigations of rhythmic exercise studies.

Tipton, "Exercise, Training and Hypertension: An Update", *Exerc. Sport Sci., Rev.*, vol. 19, Ch. 13, 1991, pp 447–505, is one of the most comprehensive recent reviews of the state of the art on the effect of exercise on blood pressure. At page 473, Tipton refers to a study which included "circuit training" which has a significant isometric component and which showed a lowering of blood pressure. The author also refers to one of his own studies with rats which were made to perform a type of isometric exercise in which the rats "unexpectedly" did not experience an increase in blood pressure as the authors had predicted would happen.

Thus, the art makes clear that a lowering of resting blood pressure is beneficial to humans in general and is particularly important to those humans who are hypertensive. While isometric and rhythmic (or dynamic) exercise is beneficial to humans in general, the isometric component of exercise, according to the foregoing art, appears to contribute more significantly to the lowering of resting blood pressure. The present invention indeed confirms such speculation in the art by disclosing an apparatus and isometric method for safely reducing the resting blood pressure of humans. The present invention has been reported in "Isometric Exercise Training Lowers Resting Blood Pressure", *Med. Sci. Sports Exerc.*, 24 (7):749–754, 1992. The disclosure of all of the foregoing publications are expressly incorporated herein by reference.

BROAD STATEMENT OF THE INVENTION

The present invention is directed in one aspect to a method for lowering the resting systolic and diastolic blood pressures of patients. This method commences with a determination of the maximal isometric force which can be exerted by a patient with any given muscle (e.g., skeletal muscle or group of muscles) of such patient. The determined maximal isometric force is recorded. The patient, then, is periodically permitted to intermittently engage in isometric contraction of the given muscle at a fractional level (e.g. up to about 60%) of the maximal force determined for a given contraction duration followed by a given resting duration. A perceptible indicia correlative to the isometric force exerted by the given muscle is displayed to the patient so that the patient can sustain the given fractional level of maximal force.

A representative procedure for a patient to follow includes the patient exerting a squeezing force with either hand equal to about 50%±5% of the previously determined maximal isometric force and holding that 50% force for 45 seconds; resting for one minute; exerting a force with the other hand equal to 50% of the maximum for 45 seconds; resting one minute; exerting a force of 50% of maximum for 45 seconds again with the first hand; resting one minute; and exerting a force of 50% for 45 seconds again with the second hand. This completes the isometric exercise for that day. The same procedure should be followed by the patient at least five days per week.

As another aspect of the present invention, disclosed is an apparatus for use by a patient in lowering the resting systolic and diastolic blood pressure of the patient. This apparatus includes the dynamometer for a patient to activate with a given muscle (e.g., skeletal muscle or group of muscles). A memory is connected to the dynamometer for recording the maximal isometric force which can be exerted by the patient with any given muscle of that patient. A display is connected to the dynamometer and to the memory for displaying percentages of the recorded maximal isometric force when the patient activates the dynamometer with the given muscle. A timer is provided for the patient to ascertain the duration over which the given muscle exerts isometric force through the dynamometer and the duration between exertions.

Advantages of the present invention include a recognition with proof that isometric exercise alone is effective for a patient to lower both resting systolic and diastolic blood pressure. Another advantage is that the lowering of resting blood pressure can be achieved utilizing isometric exercise far short of maximal force which could cause blood pressure excursions to levels dangerous, especially for hypertensive patients. Yet another advantage is an isometric exercise regimen that takes but a few minutes a day and yet which is effective in lowering the patient's resting blood pressure. A further advantage is an apparatus which has been designed to implement the isometric exercise regimen disclosed herein. These and other advantages will be readily apparent to those skilled in the art based upon the disclosure contained herein.

BRIEF DESCRIPTION OF THE DRAWINGS

The drawings will described in detail below.

DETAILED DESCRIPTION OF THE INVENTION

As the present invention demonstrates, the isometric component of exercise alone can be used to lower the resting blood pressures (both systolic and diastolic blood pressures) of patients by following a simple, yet effective, regimen that includes exerting fractional isometric force by any given muscle (for present purposes, "muscle" includes any skeletal muscle or group of muscles) for a given duration followed by a given duration of resting. This sequence is repeated several times (say, from about 3 to 6 times) and the entire regimen is repeated several times per week (say, from about 3 to 7 times per week). In as short as about one month, the patient's resting blood pressure will decrease. Since the regimen takes only several minutes per day to complete, it is believed that patients will be better able to stay with the program and, thus, receive long term benefits of lower blood pressure which has been shown to reduce incidence of mortality. This benefit is especially important to hypertensive patients. Moreover, since the patient exerts only a fraction of the maximal force of the given muscle, the patient's blood pressure during the exercise protocol does not rise to unacceptably high values whereat the patient's health would be at risk. Again, this is a major benefit of the present invention. Cessation of the regimen leads to a rise in the resting blood pressure, at least in the short term. Long term use of the regimen with assessment of the long term effects have not yet been completed. Nevertheless, it is reasonable to assume that once the patient has received the benefits of lower blood pressure from the regimen, the patient may be able to then switch to a maintenance protocol and still maintain a stable, yet low, blood pressure. Again, a study to confirm this assumption has not yet been completed.

Also disclosed is a simple, yet highly effective hand grip dynamometer which the patient can use to execute the novel regimen disclosed herein. While such devices can be adapted for other skeletal muscles or muscle groups, use of a hand grip device makes for a small, compact device that most patients can readily use. Indeed, with the advent of microcomputers, it is quite conceivable that the patient could use the device at home, at the office, or other convenient location, and then report to a physician who could download the data from the device and assess/correlate the patient's degree of compliance with the regimen and success thereof in lowering the resting blood pressure. In this regard, preliminary testing has revealed that the systolic and diastolic blood pressures each are lowered by the invention and to about the same degree.

The benefits realized by the present invention, however, can be better understood by reference to the following examples, which should be construed as illustrative and not limiting.

EXAMPLE I

Subjects

Healthy volunteers, ages 20–35, were initially screened by measuring their resting seated blood pressures twice a week for two weeks by standard auscultatory techniques. The four screening measurements were averaged and subjects were selected for resting diastolic blood pressure (DBP) in the 80–90 mm Hg range, then randomly placed into one of two groups. The experimental group (E) began with 10 subjects, of whom 8 completed the study. The control group (C) began with 10 subjects, of whom 7 completed the study. The reduction in numbers of subjects from those beginning the study were in all cases due to non-attendance. Subjects were asked to maintain the same exercise, nutritional habits, and general activities during the period of their participation in the study. The importance of not changing habits was specifically discussed with each subject. The subjects were encouraged not to change diet, stop or start smoking or consuming alcohol, or initiate other major lifestyle changes. If this was not possible, they were to inform the investigators and voluntarily withdraw from the study without prejudice. All protocols were in accordance with policy statements of the American College of Sports Medicine.

Measurements

Subjects came to the laboratory within one hour of the same time each day for their isometric exercise training or for blood pressure measurements without training (control group). Blood pressure was measured twice in the nondominant arm after at least 10 minutes seated rest and within 5 minutes of starting a hand grip exercise. Blood pressure was measured by auscultation using a mercury sphygmomanometer and stethoscope following criteria recommended by the American Heart Association Postgraduate Education Committee. Kirkendall, et al., "Recommendations for Human Blood Pressure Determination by Sphygmomanometers", *Circulation*, 62:1145A–1155A, 1980. A permanent record of blood pressure also was obtained with a cuff microphone and an electrosphygmomanometer preamplifier with a Grass Model 7D Polygraph (Grass Instruments, Quincy, Mass.). Diastolic blood pressure was taken as Korotkoff phase V (disappearance of sound). In each study all blood pressure measurements were taken by the same individual. Heart rate was determined from electrocardiographic recordings, using the Grass polygraph. Counts were made for each appropriate 30 second interval and expressed as beats/min.

Hand grip tensions were recorded from a hand grip dynamometer with a linear output related to tension using a low-level DC preamplifier and the Grass Polygraph. The subjects viewed their isometric force production on a direct-reading voltage display meter connected to the dynamometer. This provided the feedback necessary for the individuals to maintain the appropriate percentage of tension. The dynamometer has been previously described in detail. Clarke, et al., "The Duration of Sustained Contractions of the Human Forearm at Different Muscle Temperatures", *J. Physiol.*, 143:454–473, 1958 and Lind, et al., "Local and Central Circulatory Responses to Sustained Contractions and the Effect of Free or Restricted Arterial Inflow on Post-Exercise Hyperaemia", *J. Physiol.*, 192:575–593, 1967. Each day, a subject would exert a maximal effort for less than 2 seconds on the dynamometer. After at least 3 minutes rest, another effort was made. If these differed by no more than 5%, the greater tension was taken as the maximum voluntary contraction (MVC) for the day. If >5% difference occurred, additional grip tensions were measured, with rests between, until a reliable MVC measurement was obtained. The target for tensions which would elicit the appropriate fraction of the maximum (% MVC) then was displayed so that subjects could produce the appropriate tension during the experiments.

Protocol 1

One minute after completion of resting blood pressure measurements for the day, subjects began the first of 4 two-minute contractions at 30% MVC with the dominant arm. The previously established target tension representing 30% MVC was displayed on a large meter in front of the subject. They were coached to maintain an effort that enabled them to hold a steady tracking on the target meter. Three minutes rest was allowed between each of the 4 successive contractions, all with the dominant arm. The choice of this protocol was based on previous studies in which contractions were held to the point of fatigue. Wiley, et al., "Respiratory Responses to Sustained Static Muscular Contractions in Humans", *Clin. Sci.*, 40:221–234, 1971. In contradistinction, the invention is based on a training effort and duration that would modestly, rather than dramatically, raise blood pressures, and that would allow sufficient recovery time between contractions. To document the magnitude of pressure increases during the interrupted contractions, pressures were measured within the last 20 seconds of the first and fourth two-minute contractions. Adequate recovery meant that even the fourth two-minute contraction would not result in significant ischemic pain in the arm. The 4 sets of two-minute contractions and three-minute rests were tested in preliminary trials with a few subjects (not reported here) to verify that the above criteria were met. Recovery blood pressures and heart rates were monitored for 5 minutes, within which time all returned to baseline levels.

This exercise regime was scheduled for 3 days/week for 8 weeks. Any subject who missed 3 consecutive appointments for a total of 4 for the study was discontinued from the study. The criterion resulted in discontinuing 2 of 10 original subjects in the E group and 3 of 10 in the C group.

Statistics

For each subject, means of the two resting measurements taken prior to hand grip were calculated for each day's systolic and diastolic pressures. Heart rates also were measured during each resting period. Since the resting measurements on the first experimental day had not been preceded by any hand grip exercise, these measurements were used to compute the initial averages for each group. The data then were prepared for statistical analysis by computing weekly averages for each subject. The statistical treatment of this data consisted of a two-day repeated measures analysis of variance (Neter, et al., *Applied Linear Statistical Models*, 3rd Ed., Irwin, Inc. 1990) followed by a Tukey's multiple comparisons procedure. Primary factors in the analysis of variance were groups (2 levels) and weeks (8 levels) with subjects nested within groups. A significant group by week interaction measured at the 0.05 level of significance established that the 2 groups have different effects over the weeks of the study. The Tukey procedure identified which weekly means were significantly different within each group and which weekly means were significantly different when comparing the 2 groups.

Results

Resting Blood Pressure Responses

Figure 1A:
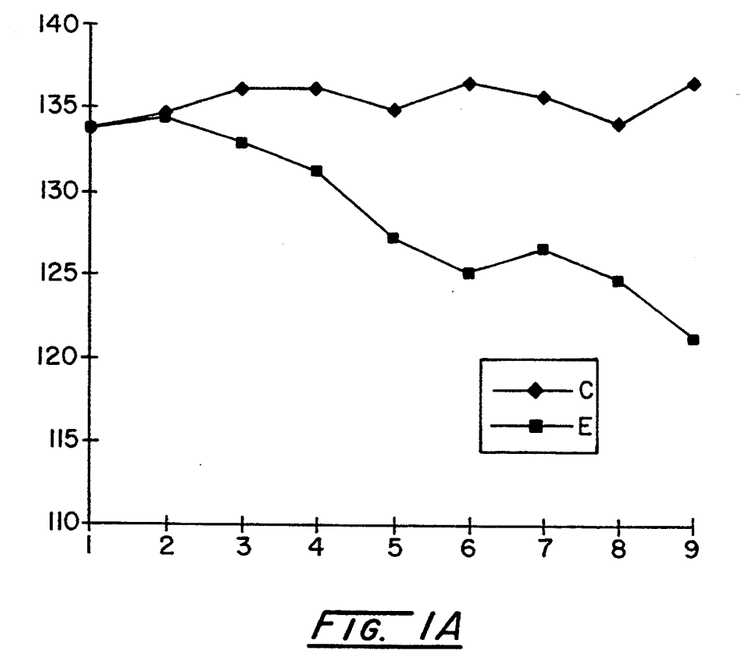
FIGS. 1A and 1B graphically display the systolic and diastolic blood pressures of control and experimental patients in the study reported in Example I.
Figure 1B:
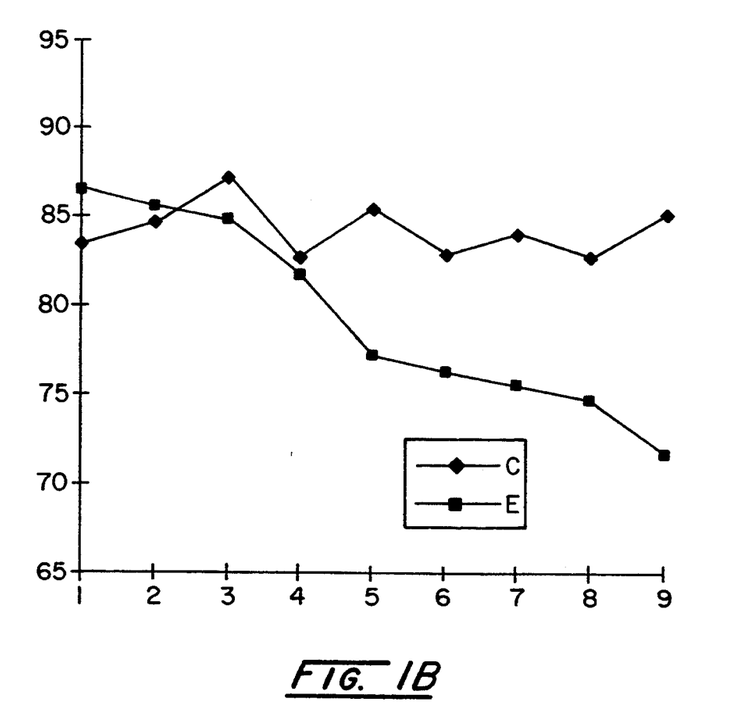

The initial systolic and diastolic blood pressures, as well as the average weekly mean blood pressures for each group, are displayed in Table 1 below and graphically in FIG. 1.

first week, both blood pressure measurements for the treatment group had become significantly lower in the fourth week. It further was determined that systolic pressure in the eighth week was significantly lower than that of the fourth week.

Exercise Blood Pressure Responses

Blood pressures in the final 30 seconds of the first two-minute contraction for the 10 subjects who started in the trained group were compared with their resting pressures. Mean increases were systolic pressures of 16.8±1.01 mm Hg (SE) and diastolic pressures of

TABLE 1A

| No | * | Rest | Week 1 | Week 2 | Week 3 | Week 4 | Week 5 | Week 6 | Week 7 | Week 8 |
|---|---|---|---|---|---|---|---|---|---|---|
| | | | | | Systolic Blood Pressure | | | | | |
| 1 | C | 146 | 140.677 | 142.000 | 132.500 | 134.669 | 137.000 | 136.333 | 134.000 | 138.000 |
| 2 | C | 138 | 126.00 | 126.000 | 130.333 | 128.000 | 139.000 | 128.333 | 129.000 | 131.000 |
| 3 | C | 135 | 133.000 | 129.333 | 131.000 | 131.667 | 129.667 | 130.333 | 129.333 | 130.000 |
| 4 | C | 121 | 131.667 | 138.667 | 137.667 | 140.667 | 139.000 | 139.000 | 136.000 | 134.000 |
| 5 | C | 135 | 141.333 | 143.667 | 138.333 | 139.669 | 141.000 | 145.500 | 148.500 | 152.000 |
| 6 | C | 124 | 136.000 | 135.667 | 131.333 | 133.000 | 133.333 | 132.667 | 128.333 | 135.000 |
| 7 | C | 139 | 134.333 | 137.667 | 134.000 | 136.667 | 136.333 | 138.000 | 134.500 | 136.000 |
| 8 | E | 138 | 143.333 | 135.000 | 129.667 | 127.500 | 127.333 | 129.667 | 124.333 | 123.667 |
| 9 | E | 131 | 130.000 | 132.667 | 131.000 | 126.667 | 125.000 | 126.667 | 126.333 | 119.667 |
| 10 | E | 131 | 128.333 | 126.667 | 122.000 | 122.333 | 116.667 | 118.000 | 116.333 | 113.000 |
| 11 | E | 136 | 137.000 | 134.000 | 133.333 | 129.667 | 124.000 | 126.000 | 127.500 | 124.000 |
| 12 | E | 136 | 140.000 | 136.333 | 134.333 | 130.667 | 130.333 | 128.667 | 126.667 | 124.333 |
| 13 | E | 136 | 133.000 | 131.333 | 128.000 | 123.333 | 123.667 | 132.333 | 124.667 | 122.000 |
| 14 | E | 131 | 130.667 | 135.333 | 136.000 | 126.500 | 123.667 | 123.333 | 123.000 | 120.500 |
| 15 | E | 132 | 132.667 | 132.333 | 136.333 | 131.000 | 130.667 | 128.000 | 129.333 | 123.667 |
| Av. | C | 134 | 134.716 | 136.143 | 136.167 | 134.905 | 136.476 | 135.738 | 134.238 | 136.571 |
| Av. | E | 133.9 | 134.375 | 132.958 | 131.333 | 127.208 | 125.167 | 126.583 | 124.771 | 121.354 |

* C is a control subject.
E is an experimental subject.

TABLE 1B

| No | * | Rest | Week 1 | Week 2 | Week 3 | Week 4 | Week 5 | Week 6 | Week 7 | Week 8 |
|---|---|---|---|---|---|---|---|---|---|---|
| | | | | | Diastolic Blood Pressure | | | | | |
| 1 | C | 93 | 93.000 | 97.667 | 84.000 | 94.667 | 85.667 | 90.000 | 87.000 | 86.000 |
| 2 | C | 82 | 88.000 | 92.000 | 93.000 | 86.333 | 87.000 | 85.000 | 84.667 | 91.000 |
| 3 | C | 82 | 78.333 | 74.333 | 76.000 | 77.333 | 76.667 | 76.333 | 75.667 | 74.000 |
| 4 | C | 83 | 84.000 | 86.667 | 86.000 | 90.000 | 88.000 | 83.667 | 85.333 | 80.000 |
| 5 | C | 79 | 91.333 | 93.333 | 89.333 | 87.333 | 89.500 | 89.500 | 84.500 | 93.000 |
| 6 | C | 83 | 78.667 | 82.667 | 71.667 | 78.000 | 72.333 | 82.000 | 81.000 | 86.000 |
| 7 | C | 82 | 80.000 | 83.667 | 79.333 | 84.333 | 81.667 | 82.000 | 81.000 | 86.000 |
| 8 | E | 96 | 105.000 | 101.000 | 100.667 | 92.000 | 89.667 | 92.333 | 86.667 | 88.000 |
| 9 | E | 91 | 87.000 | 89.667 | 84.333 | 84.333 | 86.000 | 81.667 | 84.333 | 80.000 |
| 10 | E | 79 | 77.000 | 73.000 | 69.333 | 62.333 | 61.667 | 62.000 | 56.667 | 58.333 |
| 11 | E | 88 | 87.667 | 84.000 | 79.333 | 72.000 | 71.333 | 68.667 | 70.000 | 59.500 |
| 12 | E | 86 | 85.333 | 91.000 | 84.667 | 80.000 | 76.667 | 78.333 | 77.333 | 72.667 |
| 13 | E | 89 | 82.000 | 78.667 | 75.333 | 74.000 | 74.000 | 72.667 | 71.667 | 69.333 |
| 14 | E | 81 | 77.667 | 81.000 | 78.000 | 75.000 | 73.667 | 72.000 | 73.333 | 69.500 |
| 15 | E | 82 | 83.000 | 80.333 | 82.333 | 78.000 | 77.333 | 77.000 | 77.667 | 75.333 |
| Av. | | 83.43 | 84.762 | 87.190 | 82.762 | 85.427 | 82.976 | 84.071 | 82.738 | 85.143 |
| Av. | E | 86.5 | 85.583 | 84.833 | 81.750 | 77.208 | 76.292 | 75.583 | 74.708 | 71.583 |

* C is a control subject.
E is an experimental subject.

Systolic measurements declined over the eight-week period in the exercise trained subjects from a group initial average of 134.1±0.95 (SE) mm Hg to 121.4±1.34 mm Hg, and diastolic measurements declined from 86.5±2.01 mm Hg to 71.6±3.50 mm Hg. For the control group, systolic pressures on the initial measurements and the last week were 134.0±3.30 mm Hg and 136.6±2.78 mm Hg, respectively, while diastolic pressures were 83.4±1.67 mm Hg and 85.0±2.43 mm Hg. As exhibited (FIG. 1 ) by the nonparallel nature of the weekly means for the two groups, there was a significantly different effect of the groups on systolic (F=1.77; P<0.0001) and diastolic pressures (F=8.78; P<0.0001). The multiple comparisons procedure revealed further that, as compared with the means for the first week, both blood pressure measurements for the treatment group had become significantly lower in the fourth week. It further was determined that systolic pressure in the eighth week was significantly lower than that of the fourth week.

15.9±0.90 mm Hg.

Resting Heart Rate Responses

Initial and final week mean sitting heart rate measurements were 78±7.87 (SE) bpm and 76±6.52 bpm, respectively, for the experimental group and 77±4.57 bpm and 82±8.26 for control group. These changes were not significantly different for either group (P>0.05).

EXAMPLE II

Subjects

Procedures were followed as described for Example I, for 10 volunteers, ages 29–52. All subjects completed the protocol. To test our hypothesis in situations closer to "normal" everyday experience, rather than a research laboratory, the investigator either met the subjects in his or her workplace or, if no routine workplace existed, in an unoccupied room near the laboratory. All subjects in this study group participated in the isometric exercise training. The lack of a control group of subjects makes this different from Example I and limits the comparison of effect of the training with the response during the detraining period in those same subjects, rather than with a matched control group.

Measurements

A portable dynamometer system was used for this study, which precluded obtaining a permanent recording of data as in Example I. The investigator visually observed dynamometer tensions and recorded them. Blood pressures were recorded from auscultatory measurements using a Hawksley Random Zero Sphygmomanometer (Hawksley and Sons Ltd., Lancing, Sussex, England), and heart rate was determined by palpation of the radial artery between blood pressure recordings.

Protocol 2

Procedures followed were like those of Protocol 1 with the following exceptions. Beginning with the right arm, 4 isometric contractions of 50% MVC were held for 45 seconds, alternating arms, with one minute rests between sets, thereby considerably shortening the time for each exercise session. Exercise sessions were performed 5 days/week over 5 weeks until 24 sessions were completed, matching the total number in Protocol 1. During weeks 6-10, no isometric exercise training was performed ("detraining phase"). Resting blood pressures and heart rate recordings were continued once per week after 10 minutes sitting at rest in the same location and the experiments had been performed.

Statistics

The data for each subject were prepared for analysis in the same manner as in Example 1. As there was no control group for Example II, a one-way repeated measures analysis of variance (week as the primary factor crossed with subjects) established a significant difference among the weekly means. Tukey's multiple comparisons procedure then showed which means differed from those of the first and last (fifth) weeks of the isometric training period.

Results

The results recorded are set forth in Table 2 below and graphically in FIG. 2.

TABLE 2A

| | | | | | Systolic Blood Pressure | | | | | | |
|---|---|---|---|---|---|---|---|---|---|---|---|
| No | Rest | Wk 1 | Wk 2 | Wk 3 | Wk 4 | Wk 5 | Wk 6 | Wk 7 | Wk 8 | Wk 9 | Wk 10 |
| 1 | 138.0 | 138.4 | 129.2 | 129.2 | 127.6 | 121.5 | 126.0 | 124.0 | 130.0 | 132.0 | 140.0 |
| 2 | 116.0 | 119.6 | 119.2 | 116.8 | 106.8 | 105.2 | 110.0 | 112.0 | 110.0 | 112.0 | 118.0 |
| 3 | 122.0 | 121.6 | 120.4 | 118.0 | 115.6 | 115.5 | 114.0 | 116.0 | 112.0 | 122.0 | 124.0 |
| 4 | 128.0 | 126.4 | 120.8 | 122.4 | 118.8 | 117.0 | 126.0 | 116.0 | 126.0 | 126.0 | 124.0 |
| 5 | 126.0 | 124.8 | 124.0 | 117.6 | 122.8 | 118.8 | 120.0 | 124.0 | 128.0 | 120.0 | 124.0 |
| 6 | 140.0 | 137.2 | 133.6 | 131.6 | 124.4 | 130.5 | 140.0 | 134.0 | 120.0 | 148.0 | 130.0 |
| 7 | 126.0 | 121.6 | 116.4 | 116.8 | 112.4 | 115.0 | 108.0 | 120.0 | 124.0 | 124.0 | 126.0 |
| 8 | 122.0 | 120.0 | 118.8 | 115.2 | 118.0 | 114.0 | 124.0 | 118.0 | 122.0 | 118.0 | 128.0 |
| 9 | 126.0 | 124.0 | 118.5 | 116.0 | 116.8 | 112.5 | 118.0 | 116.0 | 120.0 | 120.0 | 124.0 |
| 10 | 126.0 | 126.8 | 126.8 | 122.0 | 125.2 | 125.0 | 120.0 | 126.0 | 132.0 | 130.0 | 130.0 |
| Av. | | 126.0 | 122.8 | 120.6 | 118.8 | 117.5 | 120.6 | 120.6 | 122.4 | 125.2 | 126.8 |

TABLE 2B

| | | | | | Diastolic Blood Pressure | | | | | | |
|---|---|---|---|---|---|---|---|---|---|---|---|
| No | Rest | Wk 1 | Wk 2 | Wk 3 | Wk 4 | Wk 5 | Wk 6 | Wk 7 | Wk 8 | Wk 9 | Wk 10 |
| 1 | 96.0 | 93.2 | 92.0 | 90.0 | 87.2 | 85.0 | 84.0 | 88.0 | 90.0 | 94.0 | 96.0 |
| 2 | 80.0 | 81.6 | 80.0 | 75.2 | 73.6 | 74.0 | 74.0 | 72.0 | 78.0 | 74.0 | 82.0 |
| 3 | 80.0 | 81.2 | 80.8 | 79.6 | 76.4 | 75.5 | 78.0 | 78.0 | 80.0 | 82.0 | 84.0 |
| 4 | 80.0 | 84.4 | 84.4 | 83.2 | 78.8 | 77.5 | 84.0 | 83.0 | 82.0 | 80.0 | 88.0 |
| 5 | 92.0 | 88.8 | 89.2 | 83.6 | 84.0 | 81.6 | 86.0 | 86.0 | 92.0 | 82.0 | 86.0 |
| 6 | 92.0 | 87.2 | 89.6 | 84.6 | 82.0 | 81.5 | 90.0 | 80.0 | 84.0 | 84.0 | 90.0 |
| 7 | 82.0 | 83.2 | 79.6 | 78.4 | 75.6 | 74.0 | 72.0 | 76.0 | 86.0 | 86.0 | 86.0 |
| 8 | 88.0 | 82.4 | 77.2 | 77.2 | 78.0 | 73.5 | 80.0 | 76.0 | 84.0 | 76.0 | 84.0 |
| 9 | 84.0 | 82.4 | 76.0 | 76.8 | 76.4 | 70.0 | 78.0 | 74.0 | 76.0 | 78.0 | 82.0 |
| 10 | 88.0 | 84.0 | 84.8 | 78.8 | 80.0 | 80.5 | 78.0 | 82.0 | 80.0 | 84.0 | 88.0 |
| Av. | 86.2 | 84.8 | 83.4 | 80.7 | 79.2 | 77.3 | 80.4 | 79.5 | 83.2 | 82.0 | 86.6 |

Figure 2A:
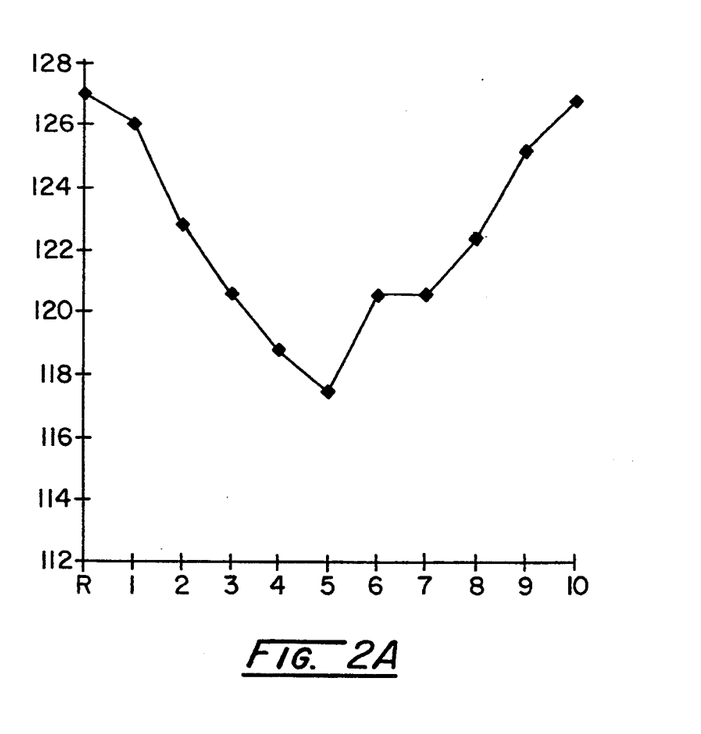
FIGS. 2A and 2B graphically display the systolic and diastolic blood pressures of experimental patients in the study reported in Example II.
Figure 2B:
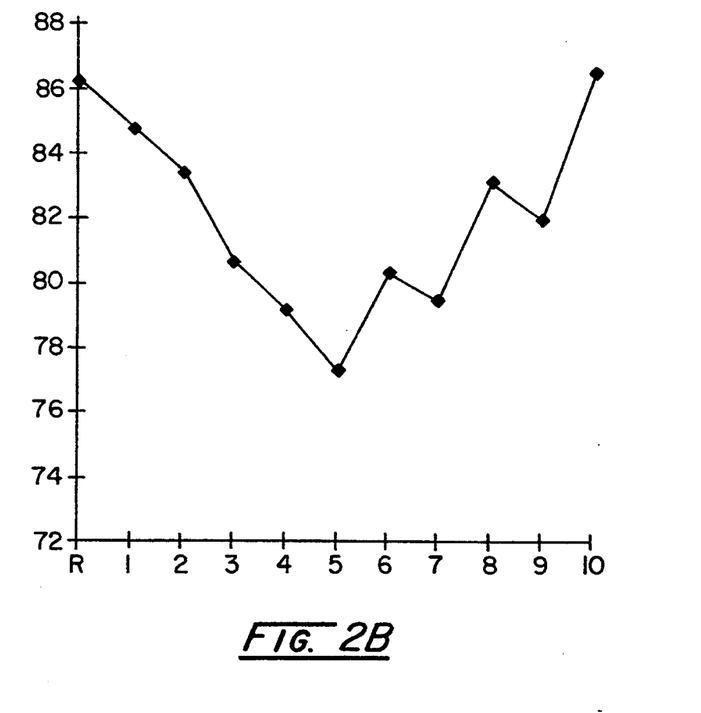
Figure 3:
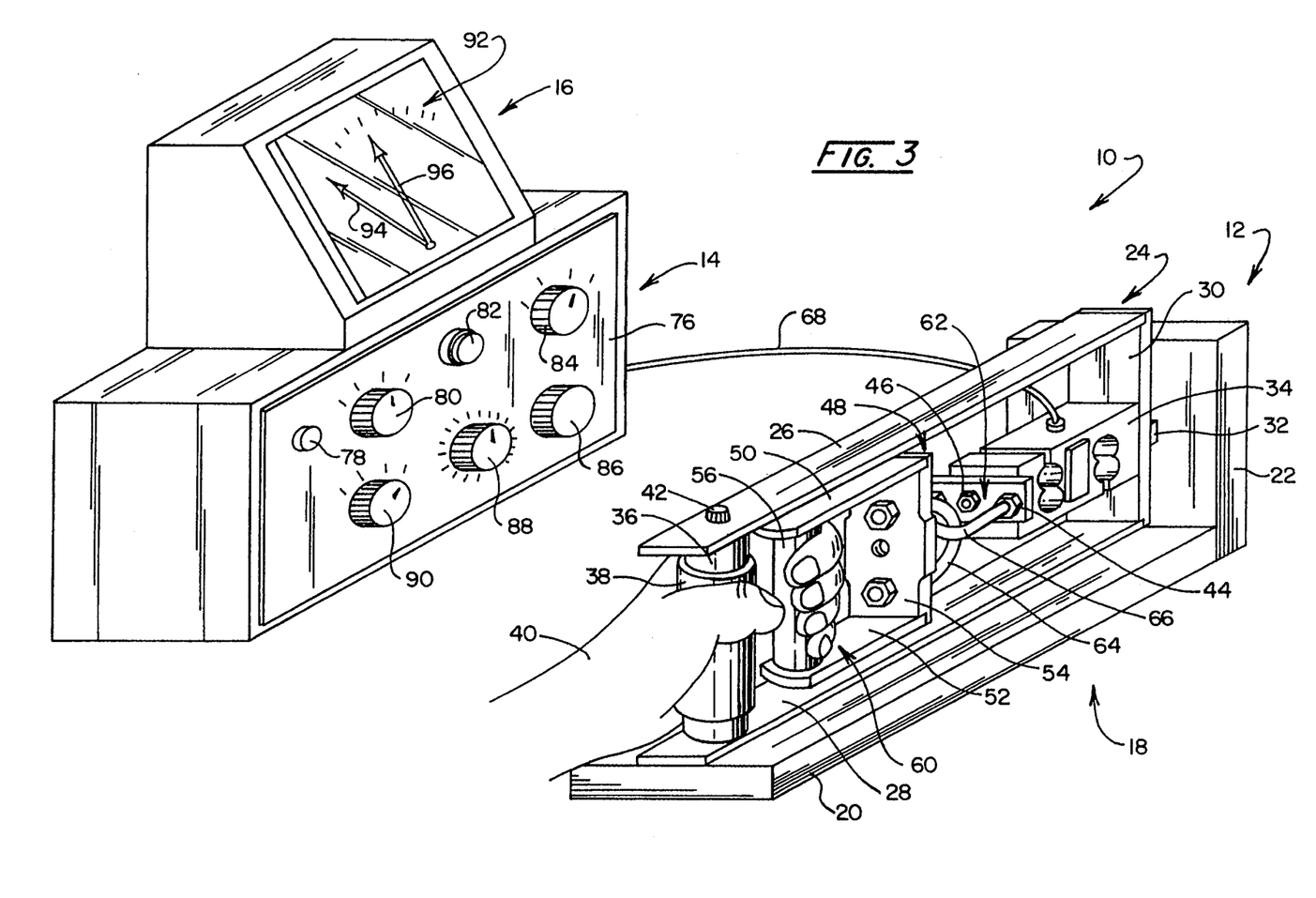
FIG. 3 is a pictorial representation of a portable dynamometer system according to the invention showing a hand grip assembly, control console, and meter.

Systolic pressures declined during the isometric training period of five weeks from $127.0 \pm 2.28$ (SE) to $117.5 \pm 2.23$, then returned during the five-week detraining period to $126.8 \pm 1.84$ (FIG. 2). Diastolic pressures showed a similar pattern, declining from $86.2 \pm 1.85$ to $77.4 \pm 1.49$ and returning to $86.6 \pm 1.34$. The changes in weekly means were statistically significant (systolic: $F = 5.73$, $P < 0.0001$; diastolic: $F = 13.06$, $P < 0.0001$). The multiple comparisons procedure determined that the systolic means were significantly lower for weeks 3-6 as compared with week 1. Diastolic means were significantly lower for weeks 3-7 as compared with week 1. As compared with the means of week 5, the systolic measurements became significantly higher in weeks 8, 9, and 10. Heart rates showed no significant changes at any point during the study ($F = 1.09$; $P = 0.377$). Referring to FIG. 3, a portable dynamometer system as employed, for instance, in connection with Example II described is pictorially represented generally at 10. System 10 includes a hand grip assembly 12 which performs in conjunction with a control console 14 and an associated meter form of readout 16. The hand grip assembly 12 is seen to include an L-shaped base support 18 including an elongate base member 20. Fixed to and extending upwardly normally from the base member 20 is a stanchion plate 22. Attached to the stanchion plate 22 is a first force transfer assembly represented generally at 24 and including upper and lower compression links shown, respectively, at 26 and 28 which, in turn, are coupled with an upstanding transverse load cell support plate 30. Plate 30 is attached to but spaced from stanchion plate 22, a spacer 32 being seen in the drawing. The latter spacer permits the connection to support plate 30 of one end of a load cell 36. Note, in this regard, that the load cell 36 is suspended between the links 26 and 28. Load cell 36 may be provided, for example, as a Model U1T marketed by Hotfinger Baldwin Measurements, Inc. of Framingham, Mass. having, for example, a rated capacity of 500 lbs and performing, in conventional fashion, with a resistor bridge form of strain gauge. Device 36 is configured to be bolted to support plate 30 at one end thereof and the opposite end extends in cantilever fashion spaced from and parallel with the compression links 26 and 28. The opposite ends of compression links 26 and 28 are seen to support a cylindrical hand grip component 36 having a rubber gripping cover 38. Grip 36 is configured for facile grasping at the thumb forefinger union of the human hand 40 and securement of the hand grip component 36 is provided by connectors, for example, the machine screw 42.

Load cell 34 additionally is connected with a rectangular load transfer plate 44, such connection being by a bolt as represented at 46 which is coupled with a threaded bore (not shown) axially aligned along the cell 34. Load transfer plate 44 is coupled with a second force transfer assembly represented generally at 48. Assembly 48 includes parallel, spaced apart and oppositely disposed upper and lower tension links shown, respectively, at 50 and 52 which are fixed to and extend outwardly from an upstanding or transverse connector plate 54. The outwardly disposed ends of links 50 and 52 serve to support a hand grip component 56 which is of cylindrical configuration and dimension as well as located with respect to component 36 to be grasped by the forefingers 60 of hand 40. The relative positioning of grips 56 and 36 is such as to facilitate the application of gripping force between them by hand 40. Second force transfer assembly 48 is connected for the purpose of applying tension to load cell 34 through a universal joint represented at 62 and formed of a U-bolt 64 which is connected to plate 54 and a freely abuttably coupled U-bolt 66 which, in turn, is bolted to plate 44. With the arrangement shown, the hand 40 may pull second transfer assembly 48 toward grip 36 to impose a tensional force upon the load cell 34 through the universal joint 62. By utilizing such a universal joint, a uniform and axially directed force vector application is achieved to improve the accuracy of the output of the load cell 34. That force output signal is provided along a flexible cable 68.

Cable 68 extends to control circuitry within console 14. Looking to the console 14, it may be observed that it includes a face plate 76 which, in turn, provides indicia and support for a series of manually actuated controls as well as a power on light 78. Looking to the manual controls, at the upper row to the left at 80 is a power switch 80 having four positions which may be designated: "external", "off", "battery check", and "battery". Next adjacent to the knob control switch 80 is a normally off instantaneous push type switch 82. Switch 82 serves to carry out a reset function. Next adjacent to switch 82 is a knob actuated switch 84 which is designated as a "mode" switch. The four positions of mode switch 84 are designated as: "tension", "peak", "set max", and "target". Beneath switch 84 is a knob actuated switch 86 which is designated as a "maximum" switch. Adjacent to switch 86 is a knob actuated switch 88 which is designated as a "target percent" switch and which is associated with indicia printed upon face plate 76 showing percentage increments, for example, ranging from 20% to 80%. Finally, a knob actuated switch 90 is provided which is designated as a "range switch" which is associated with indicia printed upon the face plate 70 indicating range values, for example, in kilograms from 10 Kg to 100 Kg.

Above the console 14, the meter 16 provides a readout in conjunction with a numerically scaled indicia represented at 92. The indicia 92 perform in conjunction with a left zeroing needle 94. Additionally formed upon the face of the meter 16 is a permanent upstanding arrow 96 which is pointed toward the center position of the indicia 92 and functions as a reference for the subject utilizing the system 10 during the above-described protocol calling for a grip representing a predetermined percentage of maximal gripping force.

Figure 4A:
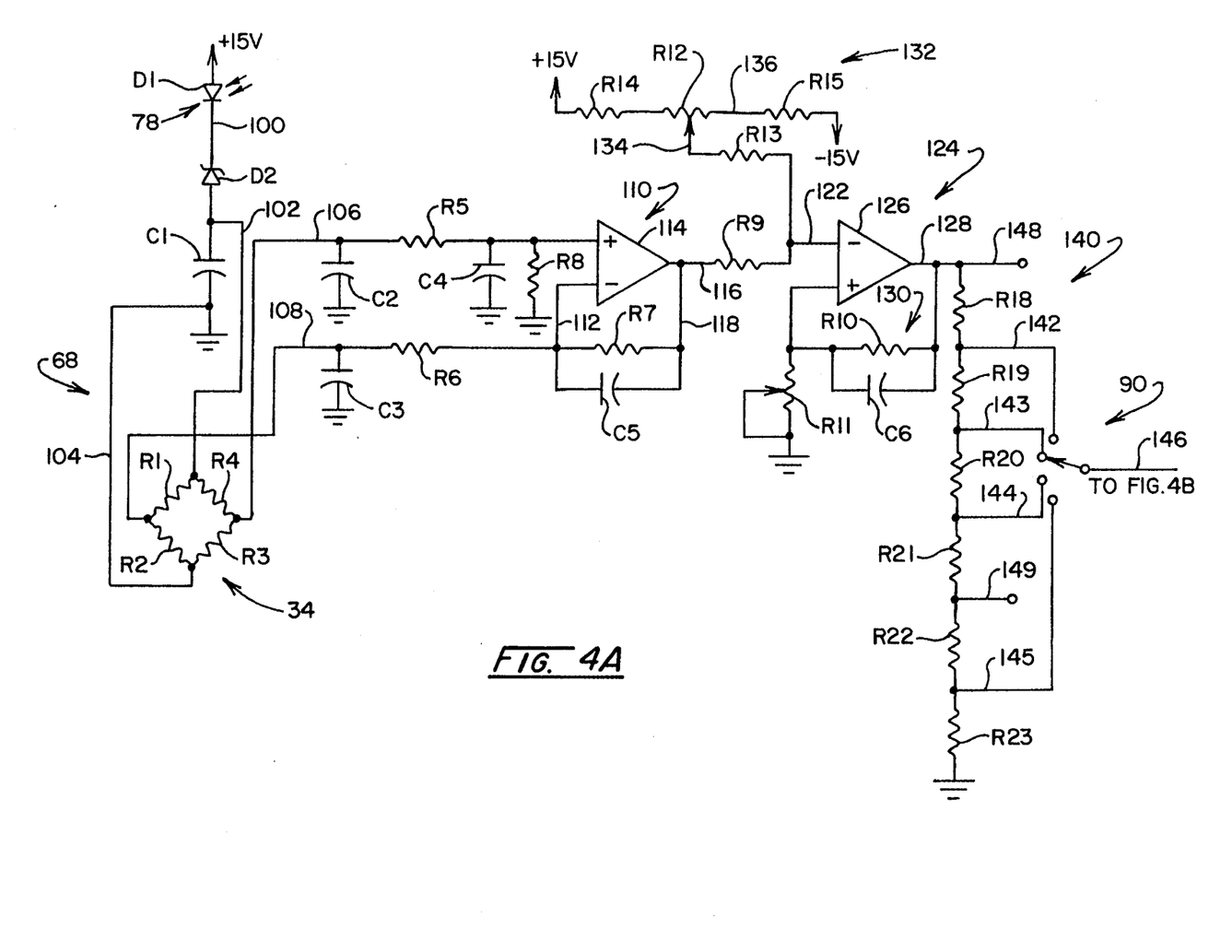
FIGS. 4A and 4B combine as labeled thereon to show an electrical schematic diagram of the sensing components, readout, and control features of the system of FIG. 3.
Figure 4B:
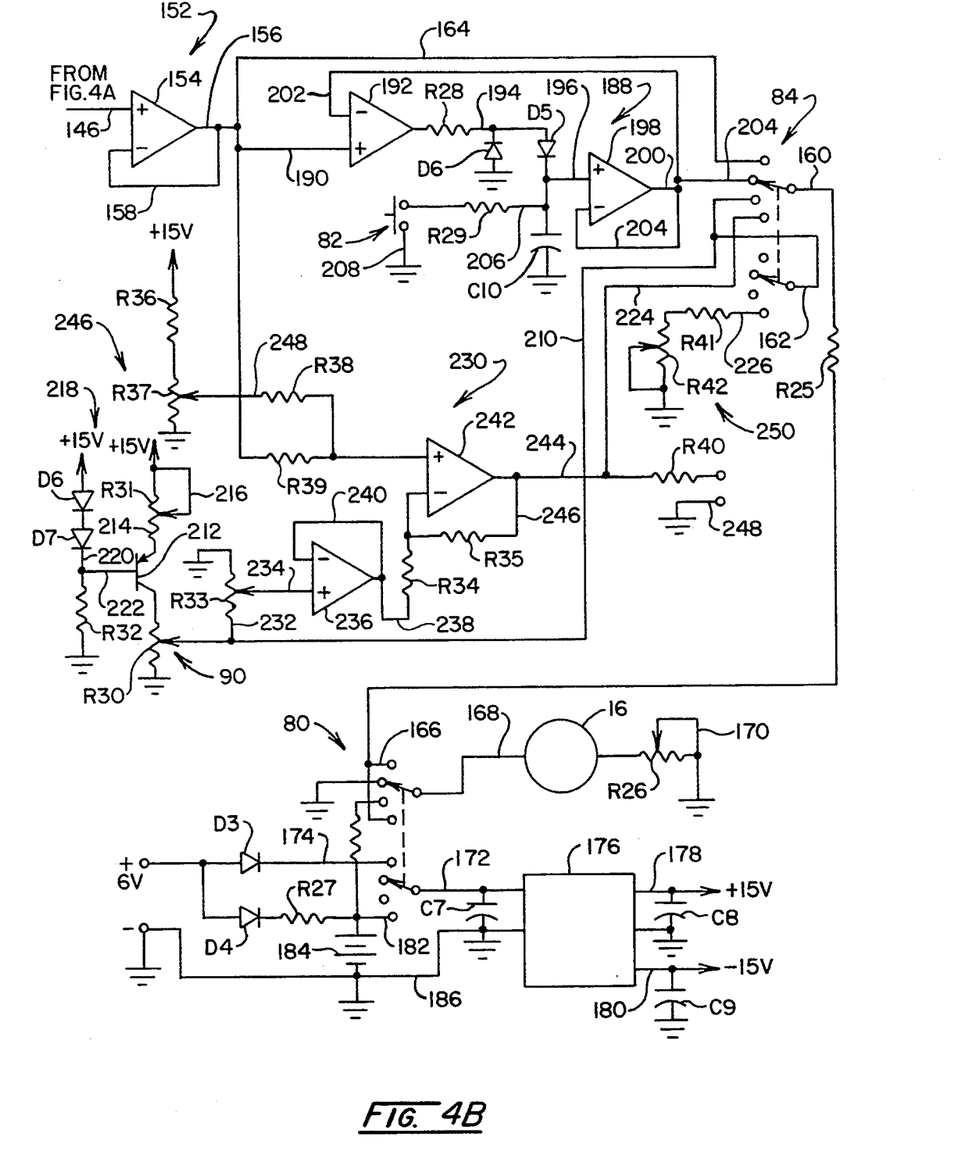

Referring to FIGS. 4A and 4B, which should be associated in the manner indicated by the labeling thereon, the control circuit associated with the console 14 and load cell 34 is depicted. Looking particularly to FIG. 4A, the power-on light 78 is represented as a light emitting diode (LED) D1 coupled within line 100 to +15 v supply. Line 100, in turn, incorporates a Zener diode D2 and is coupled via power leads 102 and 104 to the bridge configured resistive elements R1-R4 of the load cell 34. As is apparent, leads 102 and 104 form a part of the cable 68 as described in connection with FIG. 3. Line 100 additionally extends through filtering capacitor C1 to ground and, with the arrangement shown, the diode drop occasioned by LED D 1 and the voltage control provided by Zener diode D2 achieves a requisite nominal 10 v power supply for the load cell 34. The fourth responsive output of load cell 34 is shown provided at lines 106 and 198 which are seen to be coupled with filtering capacitors shown, respectively, at C2 and C3. Lines 106 and 108 extend to an input stage including respective resistors R5 and R6 to the inputs of a differential amplification stage represented, in general, at 110. In this regard, line 108 is seen to extend via line 112 to the inverting input of an operational amplifier 114. Device 114 may be provided, for example, as type OP-07 and has an output at line 116 to which a feedback line 118 incorporating resistor R7 is provided extending to line 112. A capacitor C5 also is incorporated within feedback path 118 for the purpose of noise control and bandwidth diminution. A resistor R8 is seen coupled between line 106 and ground. Resistors R5 and R6 are closely matched with a relatively tight tolerance of 0.1% or better. Resistors R7 and R8 are closely matched in similar fashion. Inasmuch as a single ended excitation is provided for the resistive elements of load cell 34, the output thereof will average about, for example, 5 v and the difference between the force output signals at lines 106 and 108 will, for example, be in the range of only a few millivolts. Thus, by carrying out resistor matching, a common mode rejection may be achieved at stage 110. Stage 110 provides a gain of about 100 with respect to the difference of the signal at lines 106 and 108 and the thus amplified signal at line 116 is correlative to the extent of force applied by hand 40 to the load cell 34.

The treated force correlative signal at line 116 is seen directed through a resistor R9 and thence to line 122 to the input of a gain and summing stage represented generally at 124. Formed including an operational amplifier 126 which may be of the earlier-identified type OP-07 marketed, for example, by Precision Monolithics, the output of amplifier 126 is presented at line 128 which, in turn, is coupled to a gain defining feedback path represented generally at 130 and incorporating resistor R10, noise avoidance capacitor C6, and a calibrating potentiometer represented at R11 which is actuable to adjust gain. Additionally coupled to line 16 and, correspondingly to line 122 and the input to device 126, is a zeroing network represented generally at 132 which is seen to incorporate a potentiometer R12 having a wiper arm 134, the output of which extends through resistor R13 to line 122. Potentiometer resistance component R32 is coupled within a line 136 to peripheral, range limiting identically valued resistors R14 and R15 which, in turn, are seen to be coupled, respectively, to +15 v and −15 v power supply. Zeroing network 132 provides an adjustment to accommodate for variations in the orientation of hand grip assembly 12. For example, should the assembly 12 being vertically oriented, then the weight of second force transfer assembly 48 would be imposed upon load cell 34 to detract from the accuracy of the force output signal of the device. Thus, for any given orientation of the assembly 12, the operator may adjust the potentiometer to represent a condition wherein zero or no tensional force is applied from the hand 40. Resistors R14 and R15 are of equal value and provide a range limitation to enhance the resolution or accuracy of control provided by the network 132.

The output of stage 124 is directed to a scaling network represented generally at 140 which is comprised of a resistor chain including resistors R18–R23, certain of the junctions between are which are tapped by leads 142–145 leading, in turn, to the four terminals of range switch 90. The output of switch 90 is represented at line 146. Two additional lines as seen at 148 and 149 provide for optional couplings for certain scaling regions. In general, the resistors R18–R23 are selected so as to provide a range scaling of the signal at line 128 to accommodate for the differences in gripping force capability of the subjects undergoing the protocols associated with system 10. In this regard, for example, line 142 may be elected by switch 90 to provide a 10 Kg range; line 143 may be elected by the switch to elect a 25 Kg range; line 144 may be elected by the operator to derive a 50 Kg range; and line 145 may be elected to develop a 100 Kg range. Line 148 may be selectively interconnected to provide a 5 Kg range, for example, for utilization of the assembly 12 by children. Alternately, the operator may wish a 75 Kg scaling range which would be developed from line 149. Generally, the operator will be able to judge the range setting for switch 90 by merely looking at the subject after a period of experience with the system 10. Typically, for an entrance level or new subject, a safe or larger range of 100 Kg is elected by the operator, whereupon the amount of gripping force is observed as the meter 16 and any further range adjustment then is made.

Referring to FIG. 4B, line 146 reappears as extending to a buffer stage 152. The treated signal carried at line 146 now is gripping force correlative with correction for orientation zeroing as well as ranging. Stage 152 includes an operational amplifier 154 exhibiting a high input impedance functioning to isolate or protect the range resistor chain of the scaling network 140. Provided, for example, as a type TL-071 marketed by Texas Instruments, Inc., device 154 provides a buffered output at line 156 which is seen to be coupled to the inverting input thereof via feedback line 158. The signal at line 156 is directed to a variety of functions as elected by the operator in conjunction with the operation of a two-stage mode switch represented in general in the instant figure with the earlier identifying number 84. An upper stage of switch 84 is seen coupled to line 160 while a coactuated second stage thereof is coupled with line 162. With the arrangement shown, where the mode switch is coupled to the uppermost terminal, the stage coupled with line 162 is open circuited, while the stage coupled with line 160 is connected to line 164 which receives the signal from line 156. This orientation for the switch 84 is at the earier-described "tension" position. Thus, the treated force correlative signal at line 156 is directed via line 164 and switch 84 to line 160, thence through resistor R25 to a dual stage power switch earlier described at 80 and identified by the same numeration in the instant figure. Where switch 80 is in the earlier-noted "external" orientation, then the upper stage will be coupled to line 160 via terminal 166 so as to connect the signal from line 160 via line 168 to the input of the meter earlier-described at 16 and shown by the same numeralion in the instant figure. The output of meter 16 is seen coupled through a potentiometer R26, the wiper arm of which at 170 is coupled to ground. Potentiometer R26 functions to appropriately calibrate or zero the meter 16. With the arrangement shown, the operator may read whatever force value in kilograms is developed from the hand grip assembly 12. The noted "external" orientation for the switch 80 also connects the lower stage thereof at line 172 to an external power source via line 174 incorporating an isolating diode D3 and coupled to +6 v external source which may be 6 v d.c. developed, for example, from a conventional wall plug transformer. Thus oriented, the switch 80 provides for directing the external source to a d.c.-to-d.c. converter represented at block 176 which is configured with capacitors C7–C9 to provide the circuit power supply of +15 v as represented at line 178 and −15 v as represented at line 180. Inverter 176 may be provided, for example, as a type CP4506 and functions to convert the noted 6 v to the ±15 v values. Where the power switch 80 is in the lowermost position shown, then line 160 is directly coupled to line 168 and line 172 is connected to line 182 providing for the application of battery power to the converter 176 from 6v battery supply 184 seen coupled to ground at line 186 as well as to line 182. Line 186 is seen directed additionally from the ground side of the external input and is directed to the opposite input to converter 176. With the configuration shown, the battery 184 may be charged through isolating diode D4 and resistor R27 with the application of external power.

The maximal value of force as is measured at the onset of the protocol carried out under the method hereunder is developed, for the instant embodiment, with a peak detector network represented generally at 188. This maximal force value typically will be available only for a relatively short interval of time, i.e. a fraction of a second, and will be presented again from line 156. Line 156 is seen coupled via line 164 to line 190 leading to the input stage of network 188 at operational amplifier 192. Amplifier 192 receives the treated output signals of the load cell 34 following zero adjustment and scaling, and directs them along output line 194 incorporating resistor R28 and diode D5 to a charging association with a capacitor C10. Capacitor C10 may, for example, be of a 1 microfarad polyester variety and thus is charged through active diode D5 to the highest voltage asserted therefrom for any given maximal force procedure. This voltage also is witnessed at line 196 which is directed to the non-inverting input of an operational amplifier 198. Exhibiting high input impedance, the amplifier 198 provides an output at line 200 which is coupled in feedback fashion to the inverting input of amplifier 192 via line 202. Additionally, a line 204 is connected to the inverting input of device 198. The resulting peak values as asserted at line 200 are presented at line 204 to be collected by switch 84 in the second position as shown and asserted via line 160 as earlier described through switch 80 and to the meter 16. With the voltage value representing maximal gripping force thus held pending the decay of voltage at capacitor C 10, the operator may note the value for maximal force in kilograms at meter 16 for subsequent use. Following this notation or memorization, reset switch 82 as shown in the instant drawing with the same numeration may be pressed momentarily by the operator to discharge capacitor C10 via line 206, resistor R29, and line 208 to ground during this peak value development, it may be noted that the second stage of mode switch 80 for line 162 is open circuited. In general, the switch 82 is momentarily actuated by the operator just prior to the instructions to the subject to grip the assembly 12 with maximal gripping force. This assures a zero initial condition or charging condition for the capacitor C10. Feedback line 202 aids in compensating for the voltage drop occasioned by the signal being directed through diode D5 to the capacitor C 10. Where the output of amplifier 192 drops below the value of charge at capacitor C10, then it will tend to approach negative power supply. Accordingly, a diode D6 is provided coupled between line 194 and ground for aiding the amplifier 192 in leaving a saturation state where a next voltage peak is developed. Devices 192 and 198 may be provided, for example, as type TL071.

Once the operator has noted the peak value of gripping force at meter 16, then the mode switch 84 again is actuated to the earlier-noted "set max" orientation which couples line 160 at the upper stage of the switch with line 210 and again provides for the open circuiting of the switch stage coupled with line 162. Line 210 is coupled with the wiper arm of a potentiometer represented at R30 which is knob actuated by the earlier-noted knob 90. That numeration again is represented in general in the instant figure. Potentiometer R30 is coupled to the collector of a PNP transistor 212, the emitter of which is coupled via line 214 to +15 v supply through a calibrating potentiometer represented at R31 having a wiper arm represented at line 216. Potentiometers R30 and R31 as well as transistor 212 form pan of a constant current network represented generally at 218 and additionally including cascade coupled diodes D6 and D7 coupled within line 220 which further includes a resistor R32 and is connected between +15 v supply and ground. Line 220 is tapped at line 222 which is directed to the base of transistor 212 to complete the constant current configuration. With the configuration shown, the operator maneuvers the potentiometer knob 90 while reading the meter 16 until the meter reading matches the peak or maximal force reading earlier noted or recorded. This provides an accurately developed voltage signal level corresponding with the peak reading to provide a form of analog memory for the circuit. Preferably, the knob 90 utilized. in setting the maximum value into the system is of a locking variety to avoid alteration of the value set.

Following the above procedure, the operator then maneuvers the mode switch 84 to the "target" orientation wherein line 160 is coupled with line 224 and line 162 of the second stage of switch 84 is coupled with line 226. It may be noted that line 162 is coupled with line 210 carrying the "maximum" setting provided by the operator.

With the orientation of mode switch 84 in a "target" position, the output of a subtraction network represented generally at 230 is applied to the meter 16 via line 160. Looking to network 130, it may be observed that the maximal value signal at line 210 is tapped at line 232. Line 232, in turn, is directed to a voltage divider function represented herein as a potentiometer including wiper arm 234 and a resistor function R33. Preferably, this function is provided by, for example, a 21 position switch having 5% resistive increments. This assures that upon the manipulation of the knob of device 88, a consistent resistance value is presented. Line 234 extends to the non-inverting input of a buffer stage within network 230 provided by operational amplifier 236. The output of amplifier 236 at line 238 is coupled, in conventional fashion, via a feedback line 240 to its converting input and the thus-buffered signal at line 238 is directed through resistor R34 to the inverting input of a difference amplifier developed with operational amplifier 242. The output of device 242 at line 244 is coupled via line 246 and resistor to input line 238 and the opposite input thereto is connected with a centering network represented in general at 246. Looking additionally to FIG. 3, the centering network 246 serves to modify the reading at meter 16 such that where the subject grips the assembly 12 with a force representing the targeted percentage of maximum force, then the needle 94 will be aligned with the permanent arrow indicia 96. This permits the subject to observe whether the gripping force for this subsequent stage in the protocol is above or below the targeted value which now will be represented by the vertical arrow 96. Returning to FIG. 4B, network 246 is seen to be comprised of a resistor R36 and potentiometer R37 coupled between +15 v supply and ground. The wiper arm for potentiometer R37 at line 248 is coupled to the input of amplifier 242 through resistor R38 and earlier-described line 164. Line 164, carrying the instantaneous force correlative value also provides a corresponding gripping force signal input through resistor R39 to the same input of amplifier 242. With the arrangement shown, by appropriate manipulation of arm 248, the signal from line 156 and 164 may be altered such that the output of network 230 at line 244, as directed through line 224, switch 84, and line 160 will generate a centered orientation of needle 94 of meter 16 when the target percentage developed from switch 88 is equaled by the force value at line 156. Line 244 is seen additionally to extend to an accessing terminal through resistor R40 such that additional displays and the like can be developed. The auxiliary output as developed through resistor R40 also may be provided in conjunction with an instrument ground as represented at line 248.

It may be observed that the lower stage of mode switch 84 at line 162 is connected to line 226 where the target orientation is elected by the operator.

The second or lower section of switch 84 when in the "target" mode or last position is coupled with line 226 leading to a target correction network represented generally at 250. Network 250 includes a potentiometer R42 and resistor R41. In general, during the operation of the system wherein mode switch 84 is in a "set max" orientation", the meter 16 will have drawn a modicum of current. On a subsequent maneuvering of switch 84 to the "target" orientation, that meter derived current causes a slight voltage excursion in the target percentage value. This is calibrated out of the system through factory adjustment of network 250.

Since certain changes may be made in the above method, system, and apparatus without departing from the scope of the invention herein involved, it is intended that all matter contained in the above description or shown in the accompanying drawings shall be interpreted as illustrative and not in a limiting sense.

I claim:

1. A method for lowering the resting systolic and diastolic blood pressures of a patient, which comprises the steps of:
   (a) determining the maximal isometric force which can be exerted by a patient with any given muscle of the patient;
   (b) recording the determined force in step (a);
   (c) periodically permitting said patient to intermittently engage in isometric contraction of said given muscle at a fractional level of said maximal force for a given contraction duration followed by a given resting duration; and
   (d) displaying to said patient a perceptible indicia correlative to said isometric force exerted by said given muscle based on said recorded force in step (a) so that said patient can sustain said level of force in step (c).

2. The method of claim 1, wherein said fractional level does not substantially exceed about 60% of said maximal isometric force.

3. The method of claim 2, wherein said fractional level ranges from about 30% and 50% of said maximal isometric force.

4. The method of claim 1, wherein a grip dynamometer is grasped by the hand of said patient for steps (a) and (c) of the method.

5. The method of claim 4, wherein the patient alternates hands for step (c) of the method.

6. The method of claim 5, wherein said fractional level ranges from between about 30% and 60%, the duration of isometric contraction is between about 30 and 60 seconds, the duration of resting is between about 45 and 75 seconds; which sequence is repeated twice with each hand.

7. The method of claim 6, wherein step (c) is repeated daily by the patient.

8. The method of claim 1, wherein step (c) is repeated daily by the patient.

9. The method of claim 1, wherein said perceptible indicia is one or more of a visual display, an audible display, or a tactile display.

10. Apparatus for use by a patient in lowering the resting systolic and diastolic blood pressure of said patient, which comprises:
    (a) a dynamometer for a patient to activate with a given muscle;
    (b) a memory connected to said dynamometer for recording the maximal isometric force which can be exerted by a patient with any given muscle of the patient;
    (c) a display connected to said dynamometer and said memory for displaying percentages of said recorded maximal isometric force when said patient activates said dynamometer with said given muscle; and
    (d) a timer for said patient to ascertain the duration over which said given muscle exerts isometric force through said dynamometer and the duration between exertions.

11. Apparatus of claim 10, wherein said dynamometer includes a hand grip for the patient to squeeze with a hand.

12. Apparatus for carrying out a protocol for lowering the resting systolic and diastolic blood pressures of a subject by the exertion of maximal isometric force and target isometric force with a given muscle of said subject comprising:
    (a) a load cell having a force output signal in response to the application of force thereto;
    (b) a force transfer mechanism coupled with said load cell, responsive to said isometric force applied thereto by said subject to evoke a said force output signal correlative thereto;
    (c) a readout responsive to input signals for providing a perceptible force level output in correspondence therewith; and
    (d) a control circuit having a set maximum mode and a target mode and including an input stage responsive to said force output signal to provide treated force signals;
    said control circuit being responsive in said set maximum mode to the retained value of a said treated force signal corresponding with said maximal isometric force to effect derivation of a target value as a predetermined percentage of said retained value, and further being responsive in said target mode to said treated force signals corresponding with said target isometric force and to said derived target value to derive said readout input signals.

13. The apparatus of claim 12 in which said force transfer mechanism is a gripping mechanism graspable and squeezable by said subject to apply said force to said load cell.

14. The apparatus of claim 12 in which said control means includes a peak mode and is responsive in said peak mode to said treated force signals corresponding with said exertion of maximal isometric force by said subject to retain the value thereof for at least an interval adequate to carry out said derivation of said target value.

15. The apparatus of claim 12 in which said control circuit input stage includes a ranging network manually actuable to scale said treated force signals in correspondence with exertion of maximal isometric force by said subject.

16. The apparatus of claim 12 in which said control circuit is responsive in said target mode to derive said readout input signals in correspondence with the difference between said derived target value and said treated force signals corresponding with said target isometric force.

* * * * *